United States Patent [19]

Houser

[11] Patent Number: 5,571,207
[45] Date of Patent: Nov. 5, 1996

[54] PROSTHETIC PYLON HAVING UNIFORM FLEXURE CHARACTERISTICS

[75] Inventor: Guy M. Houser, Bainbridge Island, Wash.

[73] Assignee: Model & Instrument Development Corporation, Poulsbo, Wash.

[21] Appl. No.: 308,092

[22] Filed: Sep. 16, 1994

[51] Int. Cl.$^6$ .................................. A61F 2/60; A61F 3/00
[52] U.S. Cl. ............................................................. 623/27
[58] Field of Search .................... 623/28, 27; 138/124, 138/125, DIG. 2; 482/18, 75, 76, 109

[56] References Cited

U.S. PATENT DOCUMENTS

| | | | |
|---|---|---|---|
| 2,113,826 | 4/1938 | Carpenter | 482/18 |
| 3,379,220 | 4/1968 | Kiuchi et al. | 482/18 |
| 3,491,999 | 1/1970 | Linder | 482/18 |
| 3,752,617 | 8/1973 | Burlis et al. | 138/137 |
| 4,319,750 | 3/1982 | Roy | 273/80 B |
| 4,455,022 | 6/1984 | Wright | 273/77 A |
| 4,822,363 | 4/1989 | Phillips | 623/27 |
| 4,959,073 | 9/1990 | Merlette | 623/27 |
| 4,968,545 | 11/1990 | Fellman et al. | 138/124 |
| 4,971,846 | 11/1990 | Lundy | 138/DIG. 2 |
| 5,156,631 | 10/1992 | Merlette | 623/27 |
| 5,188,152 | 2/1993 | Ogawa | 138/129 |
| 5,201,775 | 4/1993 | Arbogast et al. | 623/27 |
| 5,217,500 | 6/1993 | Phillips | 623/27 |
| 5,265,872 | 11/1993 | Tennent et al. | 273/80 B |

FOREIGN PATENT DOCUMENTS

| | | |
|---|---|---|
| 2085351 | 4/1982 | United Kingdom . |
| WO94/04102 | 3/1994 | WIPO . |

*Primary Examiner*—David H. Willse
*Assistant Examiner*—Bruce E. Snow
*Attorney, Agent, or Firm*—Seed and Berry LLP

[57] ABSTRACT

A flexible tubular prosthetic pylon is formed by resin impregnated carbon fibers. The wall of the tubular pylon has a uniform thickness over most of its length to make the pylon relatively rigid. However, an annular band of the pylon wall adjacent one end is relatively thin to form a flexible portion at that end. During fitting of the pylon, the end of the pylon opposite the flexible portion is trimmed to a desired length. Since substantially all of the flexure of the pylon occurs in the flexible portion, trimming the opposite end does not affect the flexure characteristics of the pylon. The pylon is made by table rolling layers of pre-impregnated fibers around a mandrel, with a reduced number of layers in a band adjacent one end forming the relatively thin wall. The resulting laminate and mandrel are then placed in a mold having mold surfaces that replicate the outer surface of the pylon. The mandrel is expanded radially to force the laminate against the mold surfaces, and the mold is then heated to cure the resin. Finally, the laminate and mandrel are removed from the mold, the mandrel is made to radially contract, and the mandrel is removed from inside the laminate to complete the prosthetic pylon.

25 Claims, 7 Drawing Sheets

(PRIOR ART)

PROSTHETIC PYLON HAVING UNIFORM FLEXURE CHARACTERISTICS

FIELD OF THE INVENTION

This invention relates to prosthetic devices and, more particularly, to flexible prosthetic pylons for connecting prosthetic sockets to prosthetic feet.

BACKGROUND OF THE INVENTION

Prosthetic devices have enabled amputees to regain mobility impaired by loss of a limb, to participate again in activities enjoyed before such a loss, and to participate in new activities for the first time. Moreover, with amputees fully engaging in today's active lifestyles, amputees are participating in events such as marathons, basketball, and free-style downhill skiing.

The stump of an amputee's limb is typically placed in a socket having an inter contour that conforms to the shape of the stump. A fitting mounted on the lower end of the socket is then attached to the upper end of an elongated prosthetic pylon. Finally, a prosthetic foot is bolted to the lower end of the pylon. The pylon thus serves as the structural member used to interconnect the limb socket and the prosthetic foot. Conventional prosthetic pylons have generally been constant heavy walled tubes or cylinders manufactured from either aluminum, which is quite stiff, or nylon, which is heavy and exhibits excessive flex under high loading conditions.

In order to increase the strength and reduce the weight of conventional pylons, tubular resin-impregnated fiber reinforced composite pylons have been developed. These composite pylons can be trimmed easily to any length depending upon the desired distance between the socket fitting and the prosthetic foot. However, tubular pylons, whether they are made of composite or any other material, still exhibit the disadvantage of having flex characteristics that are dependent on finished length. In other words, a shorter pylon with the same construction as a longer pylon will possess a stiffer flex characteristic than its longer counterpart. Prosthetic pylons could be manufactured in a range of wall thicknesses depending on their length to provide uniform flexure characteristics regardless of pylon length. However, tubular prosthetic pylons are typically trimmed in the field by a prosthetist during the fitting of a prosthesis on an amputee. Manufacturing pylons having different wall thicknesses or different flex characteristics for different lengths would require the prosthetist to maintain a large inventory of prosthetic pylons so that a wide variety of pylon lengths were on hand for use.

SUMMARY OF THE INVENTION

The primary object of the present invention is to provide a prosthetic pylon having uniform flexure characteristics regardless of its length.

It is another object of the invention to provide a lightweight, flexible tubular prosthetic pylon that can be field trimmed in length without changing the flexure characteristics of the pylon.

It is still another object of the invention to provide a prosthetic pylon having uniform flexure characteristics that can be manufactured using existing composite table rolling manufacturing techniques.

These and other objects of the invention are provided by a prosthetic pylon used to connect a prosthetic foot to a prosthetic socket having a cavity surrounding the lower end of a limb stump. The pylon has a relatively long rigid portion extending from a first end toward a second end, and a relatively short flexible portion adjacent the second end. As a result, substantially all of the flexure of the pylon occurs in the relatively short flexible portion. The pylon is preferably manufactured and sold in a length that is longer than the length that the pylon will be after it has been fitted to an amputee. The length of the pylon is therefore trimmed to a desired length during fitting by cutting off a length of the pylon at its first end. Cutting off part of the pylon at the first end removes part of only the rigid portion of the pylon and thus does not substantially affect the flexure of the pylon. As a result, the flexure characteristics of the pylon as perceived by the amputee is uniform regardless of how much of the pylon is trimmed during fitting.

The pylon is preferably formed by a tube having a cylindrical wall and a hollow interior, with the cylindrical wall being relatively stiff along the rigid portion and relatively compliant in the flexible portion. Although the flexure characteristics of the cylindrical wall can be varied by a variety of techniques, the flexure characteristics are preferably varied either by making the cylindrical wall relatively thick in the rigid portion and relatively thin in the flexible portion and/or by altering the structure of the cylindrical wall between the rigid portion and the flexible portion, such as by altering the angle or selection of fibers in the wall. The pylon is preferably a laminate composed of a plurality of layers of resin impregnated fibers arranged in a weave or ply. A relatively large number of the layers can be used to form the rigid portion of the pylon while a relatively small number of the layers can be used to form the flexible portion.

The prosthetic pylon is preferably made by table rolling layers of pre-impregnated fibers around a mandrel. A number of uniform or non-uniform layers are wound around a major portion of the mandrel to form the rigid portion. However, a reduced number of layers are wound around a minor portion of the mandrel adjacent its second end to form the flexible portion. The laminate and mandrel are then placed in a cavity of a mold having mold surfaces that replicate the shape of the outer surface of the pylon. The mandrel is expanded radially to force the laminate against the mold surfaces, and the mold is then heated to cure the resin. After the resin has cured, the laminate and mandrel are removed from the mold, and, after the mandrel is made to contract, it is removed from inside the laminate, thereby forming the prosthetic pylon.

DETAILED DESCRIPTION OF THE INVENTION

Figure 1:
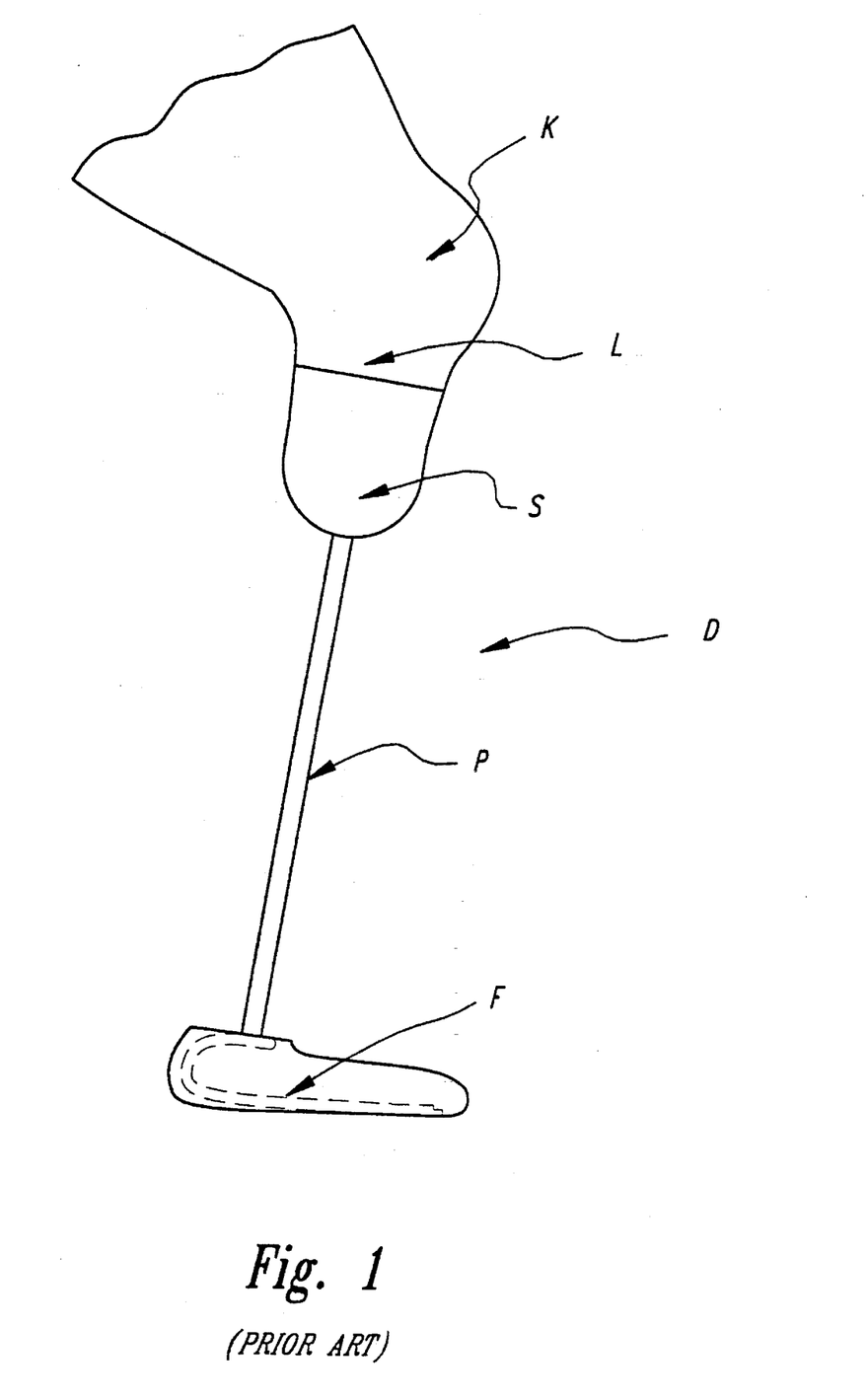
FIG. 1 is a side elevational view of a typical prosthetic pylon and foot attached to the limb stump of an amputee.

As shown in FIG. 1, a typical prosthetic device D consists of a socket S, a pylon P, and a prosthetic foot F. The socket S fits over the lower end of the stump of a limb L extending from a knee K. The pylon P attaches to a fitting on the lower end of the socket S, and the prosthetic foot F is bolted to the lower end of the pylon P. As the amputee walks or runs on the prosthetic device D, axial forces and movements are imparted to the pylon P between the prosthetic foot F and the socket S. It is generally desirable for the pylon P to flex to some degree when axial forces and torque are applied to the pylon P so that the pylon P absorbs forces that might otherwise be uncomfortably large if applied to the socket S.

Figure 2:
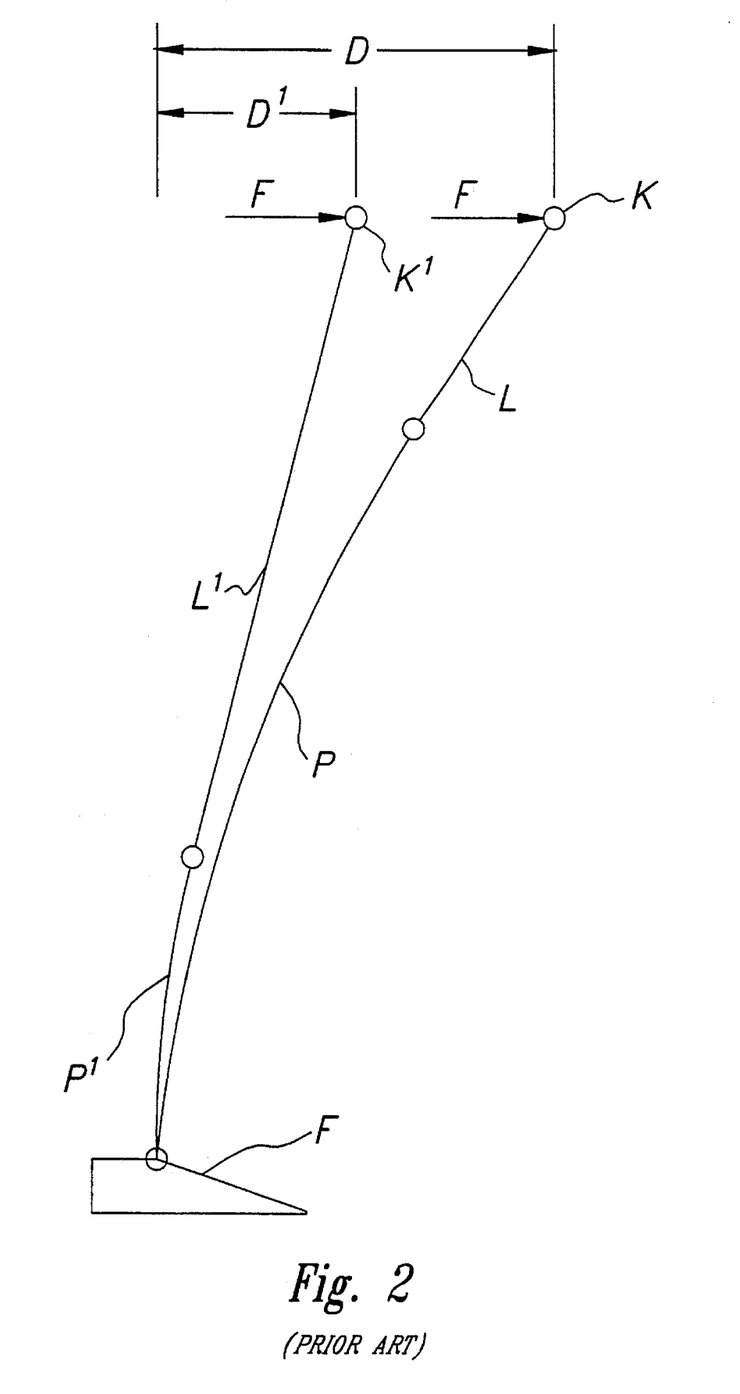
FIG. 2 is a graph showing the deflection characteristics of a conventional prosthetic pylon connecting a socket to a prosthetic foot.
Figure 3:
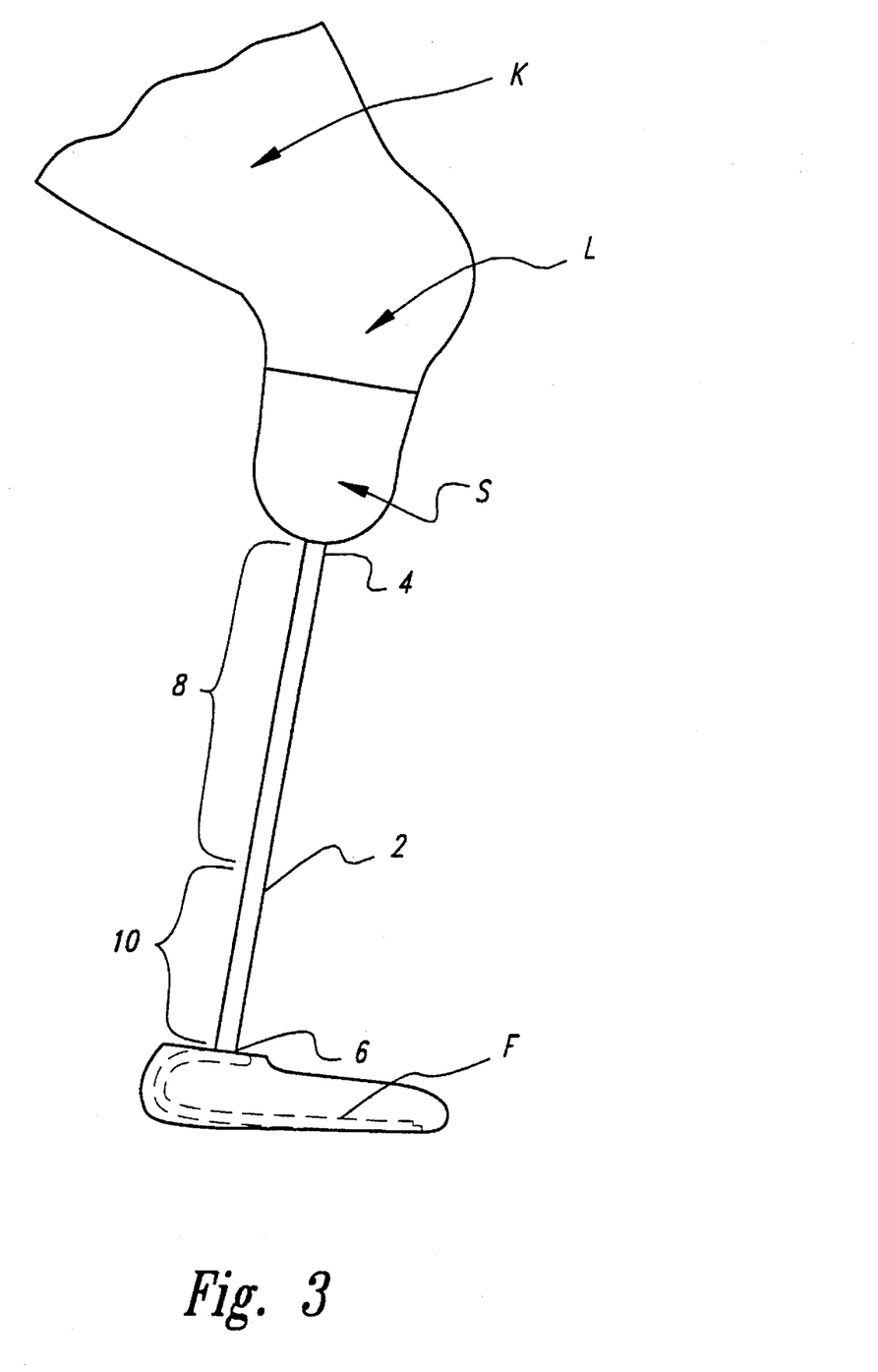
FIG. 3 is an isometric view of a preferred embodiment of a prosthetic pylon according to the present invention.

The deflection characteristics of the conventional tubular composite pylon shown in FIG. 3 for two different lengths of pylons P and P' are shown in FIG. 2, in which a force F is applied to the knee from the left. In the first case, the limb stump L is relatively short so that the pylon P must be relatively long to achieve the correct distance between the knee K and the prosthetic foot F. The relatively long length of the pylon P causes it to be relatively compliant so that it deflects a considerable distance when the force F is applied to the knee. As a result, the knee K moves a distance D responsive to the force F. In contrast, when the limb stump L' is relatively long, the pylon P' may be relatively short and still achieve the correct distance between the knee K and the prosthetic foot F. The relatively short length of the pylon P' causes it to be relatively stiff so that it deflects a relatively short distance when the force F is applied to the knee. As a result, the knee K moves only a distance D' responsive to the force F. Thus, with conventional solid or tubular composite pylons, the deflection characteristics of the pylons as perceived by the amputee at the knee K will vary depending upon the length to which the pylons P, P' are trimmed by the prosthetist during fitting. While this problem could be cured by using pylons having a variety of deflection characteristics depending upon their lengths, it would then be necessary for the prosthetist to maintain a large inventory of various pylon lengths, and their lengths would no longer be field trimable during fitting.

FIG. 3 shows a flexible prosthetic pylon 2 according to a preferred embodiment of the present invention. The pylon 2 has a first end 4 on which a conventional fitting (not shown) would be mounted for attachment to a fitting (not shown) on a socket S. A second end 6 of the pylon 2 is adapted for attachment to a prosthetic foot F such as by attaching the foot F to a conventional fitting (not shown) mounted on the second end 6 of the pylon 2 or by bolting the foot F directly to the second end 6 of the pylon 2. In the preferred embodiment of the invention, the pylon 2 has a uniform outer diameter, although it need not have a uniform outer diameter and it could be uniformly or non-uniformly tapered. Uniformity of the outside diameter does not necessarily determine the flexure characteristics of the pylon 2 which are instead determined by the thickness of the wall of the pylon 2 and/or its composition.

Although not apparent from FIG. 3, a major portion 8 of the pylon 2 extending from the first end 4 toward the second end 6 is relatively rigid and thus does not flex appreciably. In contrast, a relatively minor portion 10 of the pylon adjacent the second end 6 is relatively flexible. Thus, substantially the entire flex of the pylon 2 occurs in the flexible portion 10.

Figure 4:
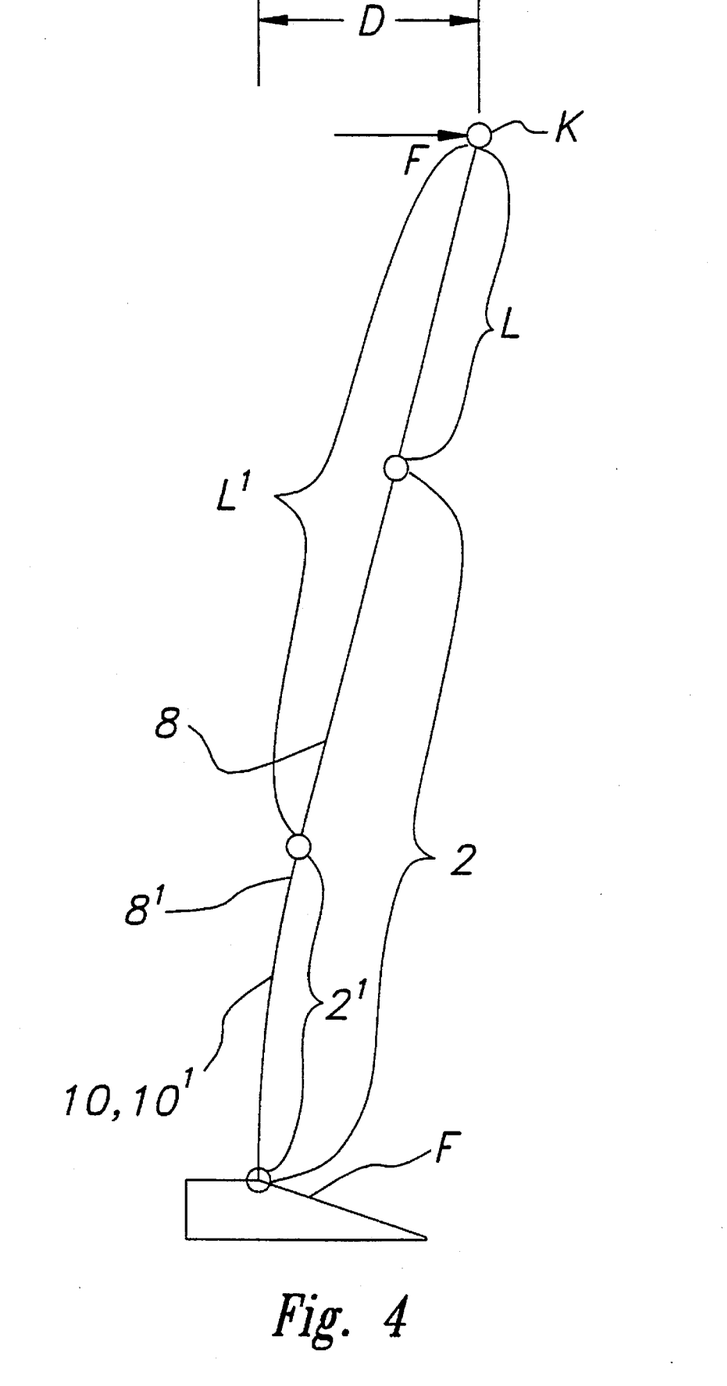
FIG. 4 is a graph showing the deflection characteristics of the inventive prosthetic pylon connecting a socket to a prosthetic foot.

The flexure characteristics of two different lengths of the inventive pylon 2 are shown in FIG. 4. In one case, the limb stump L is relatively short so that the pylon 2 must be relatively long to achieve the correct distance between the knee K and the prosthetic foot F. However, substantially all of the bending of the pylon 2 occurs in the flexible portion 10 so that the limb stump L and the rigid portion 8 of the pylon are relatively straight. When a force F is applied to the knee K, the pylon 2 flexes to allow the knee to deflect a distance D. When the limb stump L' is relatively long, the pylon 2' may be relatively short and still achieve the correct distance between the knee K and the prosthetic foot F. However, since substantially all of the bending of the pylon 2 occurs in the flexible portion 10, the pylon 2' flexes to allow the knee K to deflect the same distance D responsive to the force F as the knee K deflected when the longer pylon 2 is used. Basically, since the limb stump L and the rigid portion 8 of the pylon 2 are both relatively straight, the length of the limb stump L relative to the rigid portion 8 has no bearing on the flexure characteristic of the pylon 2, 2' as perceived by the amputee at the knee K. The flexure characteristic of the pylon 2, 2' as perceived by the amputee at the knee K will be the same regardless of the lengths to which the ends 4 of the pylons P, P' are trimmed by the prosthetist during fitting. Thus, by providing a relatively long rigid portion 8 whose length does not affect flexibility and a relatively short flexible portion 10 whose length remains unchanged, the length of the inventive pylon 2 can be adjusted without affecting the desired flexure characteristics of the pylon 2.

Figure 5:
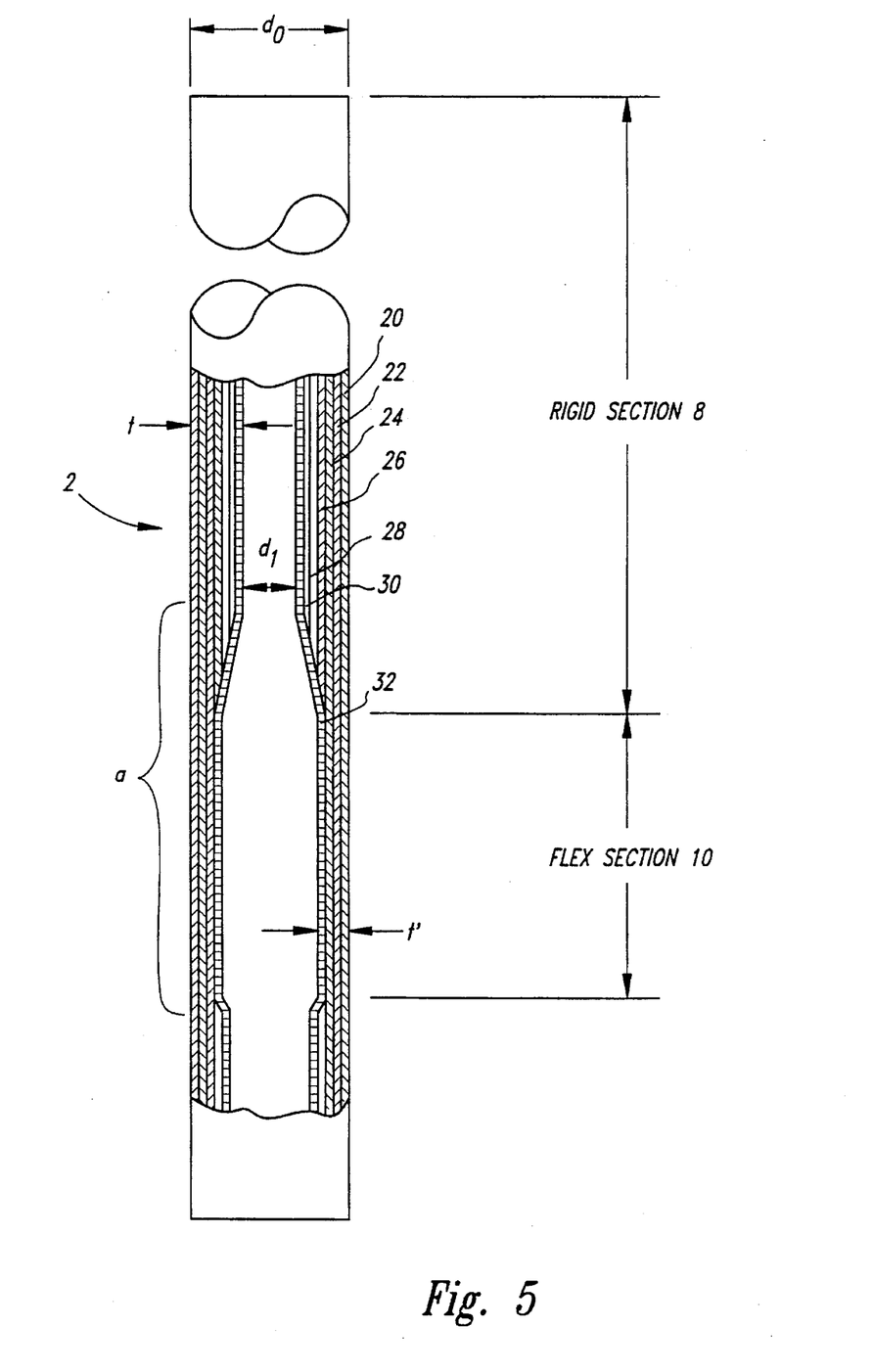
FIG. 5 is a cross-sectional view of the prosthetic pylon of FIG. 3 taken along the line 5—5 of FIG. 3.

Although the flexible portion 10 of the inventive pylon 2 can be implemented using a variety of techniques, the portion 10 is preferably made relatively flexible by making the wall of the pylon 2 relatively thin in that portion 10 and/or by altering the angle and selection of fibers in the wall of the pylon 2, as shown in FIG. 5. The embodiment of the inventive pylon 2 shown in FIG. 5 has a uniform outer diameter $d_o$, and an inner diameter $d_i$ that is increased in the area a to change the thickness of the wall of the pylon 2 from t to t' in the area a. However, it will be understood that the thickness of the wall of the pylon 2 could also be decreased in the area a by using a wall having a uniform inner diameter and an outer diameter that bulged inwardly in the area a. Also, as illustrated in FIG. 5, the angle of the fibers in the wall are varied in the area a as well as the structural composition of the wall in the area "a." Varying the angle of the fibers and their structural composition, along with making the wall of the pylon thinner, all contribute to making the pylon 2 more flexible in the area "a." Also, as mentioned above, the pylon 2 could be made relatively flexible using a variety of other techniques such as, for example, using different materials in the portions 8, 10.

The pylon 2 is preferably formed by carbon fibers and weaves pre-impregnated with a resin arranged in multiple layers 20–32, as shown in FIG. 5. The outer and adjacent three layers 20–26 are preferably pre-impregnated fibers of a material such as carbon, glass, or Vectron, with the respective layers 20–26 oriented at angles of +30°, −30°, +60°, and −60° with respect to the longitudinal axis of the pylon 2. Two stiffening layers 28, 30 of pre-impregnated 0° longitudinal plies of carbon fibers are preferably positioned adjacent the inner layer 32. The inner layer 32 is preferably a pre-impregnated hoop ply of carbon fibers oriented at 90° to the longitudinal axis of the pylon.

It will be apparent from FIG. 5 that the layers 28, 30 of 0° stiffening and one layer 26 of the flex plies in the rigid section 8 are absent from the area "a" forming the flexible portion 10, thereby contributing to the relative flexibility of this section 10. The absence of these layers 26–30 also make the wall of the pylon 2 thinner in this "a," also contributing to the relative flexibility of this section 10. Thus, the portion 10 of the pylon 2 is made relatively flexible by variations in the composition of the wall, the thickness of the wall and the angle of fibers in the wall of the flexible portion 10 relative to the rigid portion 8. However, it will be understood that other layups may also be used, and tubular pylons 2 formed by other than fiber or woven components may also be used. Also, the pylon 2 may be solid rather than tubular as long as the major portion of the pylon 2 is relatively rigid and a minor portion adjacent one end is relatively flexible.

Figures 6, 7, 8:
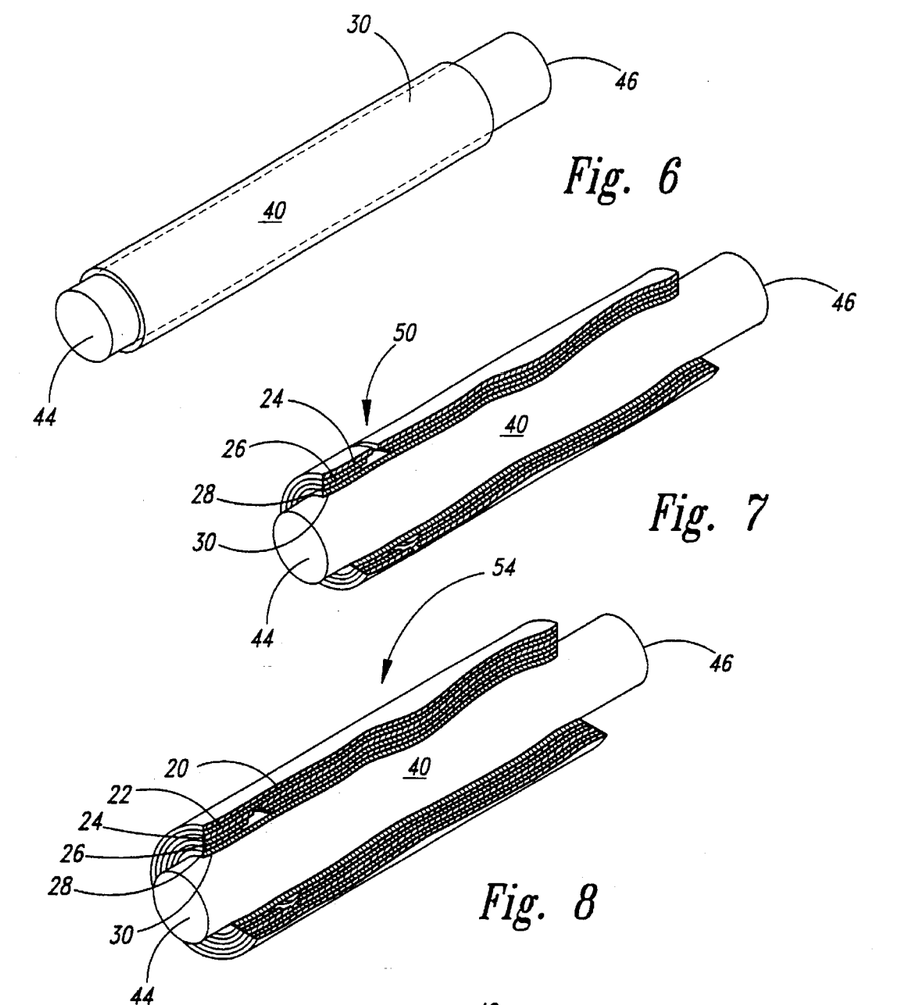
FIGS. 6–8 are schematic drawings showing a succession of steps for making the prosthetic pylon of FIG. 3.

A method of forming a pylon 2 according to a preferred embodiment of the present invention is explained below with reference to FIGS. 6–8. As shown in FIG. 6, the inner layer 32 of pre-impregnated carbon fibers is table rolled around a mandrel 40 having a first end 44 and a second end 46. The inner layer 32 extends all the way from the first end 44 to the second end 46 of the mandrel 40. The stiffening layers 28, 30 are then wrapped around the inner layer 32 except for the relatively flexible portion 10 of the pylon 2, as shown in FIG. 7. In this relatively flexible area 10, there are gaps 50 in the stiffening layers 28, 30 with the sizes of the gaps 50 decreasing from the inner stiffening layer 30 to the outer stiffening layer 28. The flex layers 20–26 are then wound around the outer stiffening layer 28, as shown in FIG. 8, to complete a laminate 54 for the pylon 2.

Figure 9:
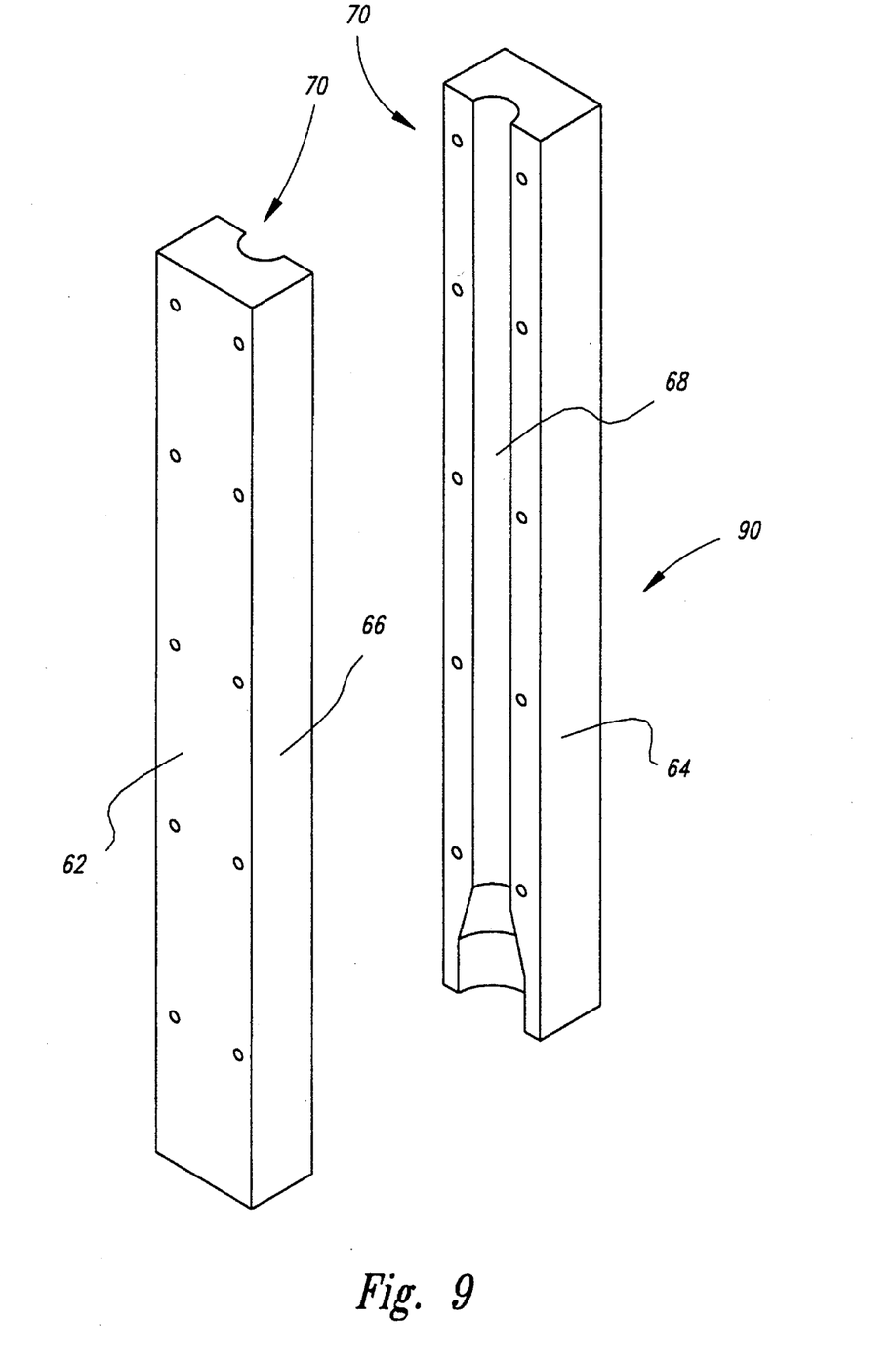
FIG. 9 is an isometric view of a clamshell mold used in manufacturing the prosthetic pylon of FIG. 3.

After the laminate 54 for the pylon 2 has been laid up as described above, the laminate 54 and the mandrel 40 that the laminate 54 surrounds are placed in a clamshell mold 60, as shown in FIG. 9. The mold 60 is formed by two mold sections 62, 64, each of which has a respective semi-cylindrical mold surface 66, 68. When the mold sections 62, 64 are joined to each other, the mold surfaces 66, 68 replicate the outer surface of the pylon 2 and form a cylindrical mold cavity 70. As explained in greater detail below, the mandrel 40 is made to expand inside the mold cavity 70 as the mold 60 is heated to cure the resin impregnating the layers 20–32. As a result, the outer surface of the outer layer 20 conforms to the mold surfaces 66, 68, and the inner layer 32 bulges outwardly into the gaps 50 in the stiffening layers 28, 30, as shown in FIG. 5. After the resin has cured, the pylon 2 is removed from the mold 60, the mandrel 40 is made to radially contract, and the mandrel 40 is then removed from the interior of the pylon 2, thereby completing the manufacturing process.

Figure 10:
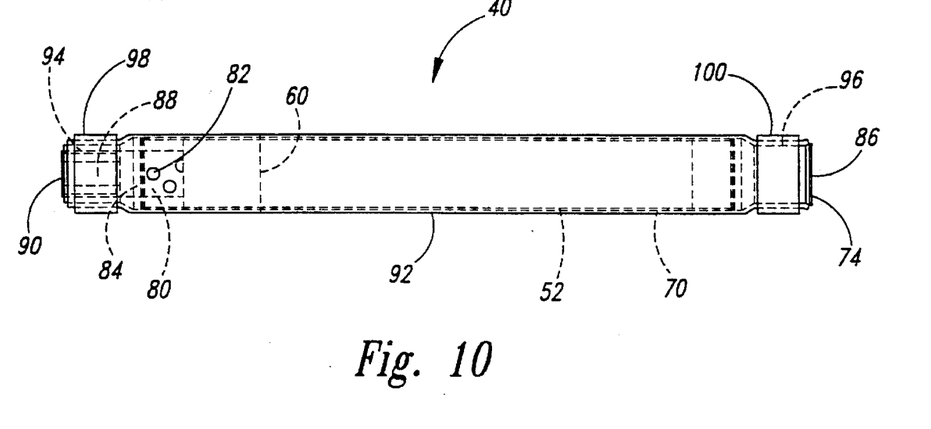
FIG. 10 is an elevational view, partially in phantom, showing an expandable mandrel used in manufacturing the prosthetic pylon of FIG. 3.

The mandrel 40 is shown in greater detail in FIG. 10. The mandrel includes a rigid tube 80 having formed therein a plurality of pneumatic holes 82 throughout its length. The tube 80 extends between a pair of cylindrical end pieces 84, 86, one of which 84 has an axial bore 88 allowing air to flow between a pneumatic port 90 in the end piece 84 and the interior of the tube 80. A resilient tube 92 extending between the end pieces 84, 86 encloses the rigid tube 80. The ends of the resilient tube 92 are held in place around cylindrical shoulders 94, 96 of the respective end pieces 84, 86 by conventional hose clamps 98, 100.

In operation, pressurized air is directed into the pneumatic port 90. The pressurized air flows through the interior of the rigid tube 80 and out of the holes 82 into the interior of the resilient tube 92, thereby inflating the resilient tube 92. The inflation of the resilient tube 92 then forces the laminate 54 (FIG. 8) against the mold surfaces 66, 68, as described above with reference to FIG. 9. After the pylon 2 and mandrel 40 are removed from the mold 60, pressurized air is allowed to flow from the pneumatic port 90, thereby allowing the resilient tube 92 to deflate and radially contract the mandrel 40.

From the foregoing, it will be evident that, although specific embodiments of the invention have been described herein for purposes of illustration, various modifications may be made without departing from the spirit and scope of the invention and the claims contained herein.

I claim:

1. A prosthetic pylon comprising an elongated cylindrical member having first and second ends, the pylon being directly or indirectly attachable at one of the ends to a prosthetic socket and being directly or indirectly attachable at the other end to prosthetic foot, said cylindrical member being relatively stiff along the major portion of its length to form a relatively rigid section and relatively compliant along a minor portion of its length adjacent said second end to form a relatively flexible section along the rain or portion of its length in which substantially all of the flexure of said pylon is concentrated so that said pylon may be trimmed to a desired length at said first end without affecting the flexure characteristics of said pylon.

2. The prosthetic pylon of claim 1 wherein said elongated cylindrical member is a tube having a cylindrical wall surrounding a hollow interior, and wherein said cylindrical wall is relatively stiff along the major portion of its length to form said relatively rigid section and relatively compliant along a minor portion of its length adjacent said second end to form said relatively flexible section.

3. The prosthetic pylon of claim 2 wherein said cylindrical wall is relatively thick in said relatively rigid section and relatively thin in said relatively flexible section.

4. The prosthetic pylon of claim 3 wherein said cylindrical wall is formed by a laminate composed of a plurality of layers of resin impregnated fibers arranged in a weave or ply.

5. The prosthetic pylon of claim 4 wherein said relatively rigid section is composed of a relatively large number of said layers, and said relatively flexible section is composed of a relatively small number of said layers.

6. The prosthetic pylon of claim 3 wherein said cylindrical wall has an outside diameter that is uniform over its entire length, and an inside diameter that is substantially uniform in said relatively rigid section and varies in said relatively flexible section.

7. The prosthetic pylon of claim 2 wherein said cylindrical wall is formed by a laminate composed of a plurality of layers of resin impregnated fibers arranged in a weave or ply.

8. The prosthetic pylon of claim 7 wherein the composition of said layers varies between said relatively flexible section and said relatively rigid section.

9. The prosthetic pylon of claim 7 wherein the angle of the fibers in a layer in said relatively flexible section is different than the angle of the fibers in a layer in said relatively rigid section.

10. The prosthetic pylon of claim 7 wherein said layers comprise a plurality of outer layers of a resin impregnated fibers with the fibers of respective layers oriented at a variety of angles relative to a longitudinal axis of said pylon, a plurality of stiffening layers of resin impregnated fibers positioned inside said outer layers for at least part of the length of said pylon with the fibers in said layers oriented parallel to said longitudinal axis, and an inner layer of resin impregnated fibers oriented perpendicular to said longitudinal axis.

11. The prosthetic pylon of claim 10 wherein said stiffening layers are present in the relatively rigid section of said pylon and absent from the relatively flexible section of said pylon.

12. The prosthetic pylon of claim 1 wherein said cylindrical member has a uniform outside diameter over its entire length.

13. A prosthetic system for a leg amputee having a limb stump, comprising:

a socket having a cavity surrounding a lower end of said limb stump;

a prosthetic foot; and a pylon having a length extending between first and second ends that are attached to said socket and said prosthetic foot, respectively, said pylon having a relatively long rigid portion extending from said first end toward said second end, and a relatively short flexible portion adjacent said second end so that substantially all of the flexure of said pylon is concentration in said flexible portion whereby the flexure characteristics of said prosthetic system as perceived by said amputee are uniform regardless of the length of said limb stump relative to the length of said pylon.

14. The prosthetic system of claim 13 wherein said pylon is formed by a cylindrical tube having a cylindrical wall surrounding a hollow interior, and wherein said cylindrical wall is relatively stiff along said rigid portion and relatively compliant along said flexible portion.

15. The prosthetic system of claim 14 wherein said cylindrical wall is relatively thick in said rigid portion and relatively thin in said flexible portion.

16. The prosthetic system of claim 15 wherein said cylindrical wall is formed by a laminate composed of a plurality of layers of resin impregnated fibers arranged in a weave or ply.

17. The prosthetic system of claim 16 wherein the composition of said layers varies between said relatively flexible portion and said relatively rigid portion.

18. The prosthetic system of claim 16 wherein the angle of the fibers in a layer in said relatively flexible portion is different than the angle of the fibers in a layer in said relatively rigid portion.

19. The prosthetic system of claim 16 wherein said rigid portion is composed of a relatively large number of said layers, and said flexible portion is composed of a relatively small number of said layers.

20. The prosthetic system of claim 17 wherein said rigid portion is composed of a relatively large number of said layers, and said flexible portion is composed of a relatively small number of said layers.

21. The prosthetic system of claim 15 wherein said cylindrical wall has an outside diameter that is uniform over its entire length, and an inside diameter that is substantially uniform in said rigid portion and increases in said flexible portion.

22. The prosthetic system of claim 14 wherein said cylindrical wall is formed by a laminate composed of a plurality of layers of resin impregnated fibers arranged in a weave or ply.

23. The prosthetic system of claim 22 wherein said layers comprise a plurality of outer layers of a resin impregnated fibers with the fibers of respective layers oriented at a variety of angles relative to a longitudinal axis of said pylon, a plurality of stiffening layers of resin impregnated fibers positioned inside said outer layers for at least part of the length of said pylon with the fibers in said layers oriented parallel to said longitudinal axis, and an inner layer of resin impregnated fibers oriented perpendicular to said longitudinal axis.

24. The prosthetic system of claim 23 wherein said stiffening layers are present in the relatively rigid portion of said pylon and absent from the relatively flexible portion of said pylon.

25. The prosthetic system of claim 13 wherein said pylon has a uniform outside diameter over its entire length.

* * * * *

UNITED STATES PATENT AND TRADEMARK OFFICE
CERTIFICATE OF CORRECTION

PATENT NO. : 5,571,207
DATED : November 5, 1996
INVENTOR(S) : Guy M. Houser

It is certified that error appears in the above-indentified patent and that said Letters Patent is hereby corrected as shown below:

In column 6, claim 1, line 20, please delete "rain or" and insert therefor --minor--.

Signed and Sealed this

Twenty-ninth Day of April, 1997

Attest:

BRUCE LEHMAN

Attesting Officer

Commissioner of Patents and Trademarks